US008133484B2

(12) United States Patent
Preiss-Bloom et al.

(10) Patent No.: US 8,133,484 B2
(45) Date of Patent: Mar. 13, 2012

(54) HEMOSTATIC MATERIALS AND DRESSING

(75) Inventors: Orahn Preiss-Bloom, Jerusalem (IL);
Ishay Attar, Haifa (IL)

(73) Assignee: Lifebond Ltd, Caesarea (IL)

( * ) Notice: Subject to any disclaimer, the term of this patent is extended or adjusted under 35 U.S.C. 154(b) by 905 days.

(21) Appl. No.: 11/978,713

(22) Filed: Oct. 30, 2007

(65) Prior Publication Data
US 2008/0213243 A1 Sep. 4, 2008

Related U.S. Application Data

(60) Provisional application No. 60/875,150, filed on Dec. 15, 2006.

(51) Int. Cl.
*A61K 38/48* (2006.01)
*C12N 9/48* (2006.01)

(52) U.S. Cl. ..................... 424/94.63; 435/212

(58) Field of Classification Search .................. 435/183, 435/212; 424/94.1, 94.63
See application file for complete search history.

(56) References Cited

U.S. PATENT DOCUMENTS

| | | | | |
|---|---|---|---|---|
| 4,572,906 A * | 2/1986 | Sparkes et al. | | 424/445 |
| 5,428,014 A | 6/1995 | Labroo et al. | | 514/12 |
| 5,525,335 A * | 6/1996 | Kitahara et al. | | 424/94.5 |
| 5,736,132 A | 4/1998 | Juergensen et al. | | |
| 5,834,232 A | 11/1998 | Bishop et al. | | |
| 5,939,385 A | 8/1999 | Labroo et al. | | 514/12 |
| 6,007,613 A | 12/1999 | Izoret | | |
| 6,054,122 A | 4/2000 | MacPhee et al. | | |
| 6,083,524 A | 7/2000 | Sawhney et al. | | 424/426 |
| 6,132,759 A | 10/2000 | Schacht et al. | | |
| 6,413,742 B1 | 7/2002 | Olsen et al. | | |
| 6,465,001 B1 | 10/2002 | Hubbell et al. | | 424/423 |
| 6,509,039 B1 | 1/2003 | Nies | | |
| 6,531,147 B2 | 3/2003 | Sawhney et al. | | 424/426 |
| 6,682,760 B2 | 1/2004 | Noff et al. | | 424/484 |
| 6,762,336 B1 | 7/2004 | MacPhee et al. | | |
| 6,992,172 B1 | 1/2006 | Chang et al. | | |
| 7,074,981 B2 | 7/2006 | Chalmers | | 602/41 |
| 7,109,163 B2 | 9/2006 | Pendharkar et al. | | 514/2 |
| 7,129,210 B2 | 10/2006 | Lowinger et al. | | 514/2 |
| 7,186,684 B2 | 3/2007 | Pendharkar et al. | | 514/2 |
| 7,208,171 B2 | 4/2007 | Messersmith et al. | | 424/422 |
| 7,241,730 B2 | 7/2007 | Hubbell et al. | | 514/2 |
| 7,285,580 B2 | 10/2007 | Stedronsky | | 523/118 |
| 7,320,962 B2 | 1/2008 | Reich et al. | | 514/21 |
| 7,435,425 B2 | 10/2008 | Qian et al. | | 424/422 |
| 7,468,350 B2 | 12/2008 | Gong et al. | | 514/2 |
| 2003/0135238 A1 | 7/2003 | Milbocker | | 606/231 |
| 2005/0129733 A1 | 6/2005 | Milbocker et al. | | 424/423 |
| 2005/0249839 A1 | 11/2005 | Ishida et al. | | 426/56 |
| 2005/0271727 A1 | 12/2005 | Kolatkar et al. | | 424/486 |
| 2006/0100138 A1 | 5/2006 | Olsen et al. | | 514/8 |
| 2006/0155234 A1 | 7/2006 | MacPhee et al. | | |
| 2006/0258560 A1 | 11/2006 | Yang et al. | | 514/2 |
| 2006/0269590 A1 | 11/2006 | Trotter et al. | | 424/445 |
| 2007/0021703 A1 | 1/2007 | McCarthy | | 602/43 |
| 2007/0082023 A1 | 4/2007 | Hopman et al. | | 424/426 |
| 2007/0128152 A1 | 6/2007 | Hadba et al. | | 424/78.27 |
| 2007/0172432 A1 | 7/2007 | Brito et al. | | 424/47 |
| 2008/0187591 A1 | 8/2008 | Rhee et al. | | 424/484 |
| 2008/0286376 A1 | 11/2008 | Qian et al. | | 424/499 |
| 2009/0175946 A1 | 7/2009 | Gaissmaier et al. | | |

FOREIGN PATENT DOCUMENTS

WO 2004028404 4/2004
WO 2008006545 1/2008

OTHER PUBLICATIONS

HemCon™ bandage (HemCon, Portland, OR) document.
Broderick EP, J Biomed Mater Res B Appl Biomater. Jan. 15, 2005;72(1):37-42).
Ito A, J Biosci & Bioeng. 2003; 95(2): 196-99.
T. Chen, J Biomed Mater Res B Appl Biomater. May 2006;77(2):416-22).
Office action for corresponding EP application 07867783.8, issued Feb. 9, 2011.
MG Tucci. (2001). J. Bioactive & Comp. Polymers. 16(2): 145-157).
B Balakrishnan et al. (2005). Biomaterials. 26(32):6335-42).
FA Weaver et al. (2002). Ann. Vasc. Surg. 16(3):286-93).
(Haug IJ, Draget KI, Smidsrød O. (2004). Food Hydrocolloids . 18:203-213).
H. Jakob et al. (1984). J. Vasc. Surg. 1:171-180).
(Werten MWT, et al. (2001). Protein Engineering. 14 (6): 447-454).
A.E. Pusateri. (2006). J. Trauma, 60:674-682.
Olsen et al, Deliv Rev. Nov. 28, 2003;55(12):1547-67).
Bertoni F, Barbani N, Giusti P, Ciardelli G. Transglutaminase reactivity with gelatine: perspective applications in tissue engineering; Biotechnol Lett (2006) 28:697-702.
Folk JE, Cole PW. Transglutaminase: mechanistic features of the active site as determined by kinetic and inhibitor studies. Biochim Biophys Acta. 1966; 122:244-64.
R. Lerner et al. (1990). J. Surg. Res. 48:165-181).
Pusateri, 2004 J Biomed Mater Res B, 15; 70(1): 114-121.
Crescenzi et al, Biomacromolecules 2002, 3, 1384-1391.
03744835.4 121 9/1494730, EP, Nov. 25, 2008.
McDermott et al, "Mechanical Properties of Biomimetic Tissue Adhesive Based on the Microbial Transglutaminase-Catalyzed Crosslinking of Gelatin", Biomacromolecules 2004, vol. 5, pp. 1270-1279.
Chen et al, "Enzyme-catalyzed gel formation of gelatin and chitosan: potential for in situ applications", Biomaterials vol. 24 (2003) pp. 2831-2841.
Chen et al, "Gelatin-Based Biomimetic Tissue Adhesive. Potential for Retinal Reattachment", Published online Nov. 8, 2005 in Wiley InterScience (www.interscience.wiley.com). DOI: 10.1002/jbm.b.30439.
Otani et al, "Effect of additives on gelation and tissue adhesion of gelatin D-poly(L-glutamic acid) mixture", Biomaterials vol. 19 (1998) pp. 2167 to 2173.
Nomura et al, "Improvement of Shark Type I Collagen with Microbial Transglutaminase in Urea", Biosci. Biotech. Biochem, vol. 65, 2001, pp. 982-985.

* cited by examiner

*Primary Examiner* — Ruth Davis

(74) *Attorney, Agent, or Firm* — D'vorah Graeser; Graeser Associates International

(57) ABSTRACT

An adhesive material comprising gelatin and a non-toxic cross-linking material such as transglutaminase. The adhesive material is useful for medical purposes as hemostatic products. The hemostatic products are useful for the treatment of wounded tissue.

15 Claims, 9 Drawing Sheets

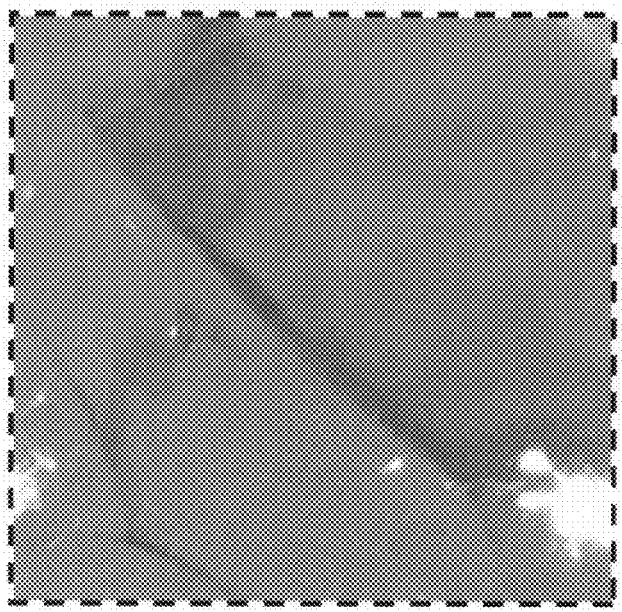
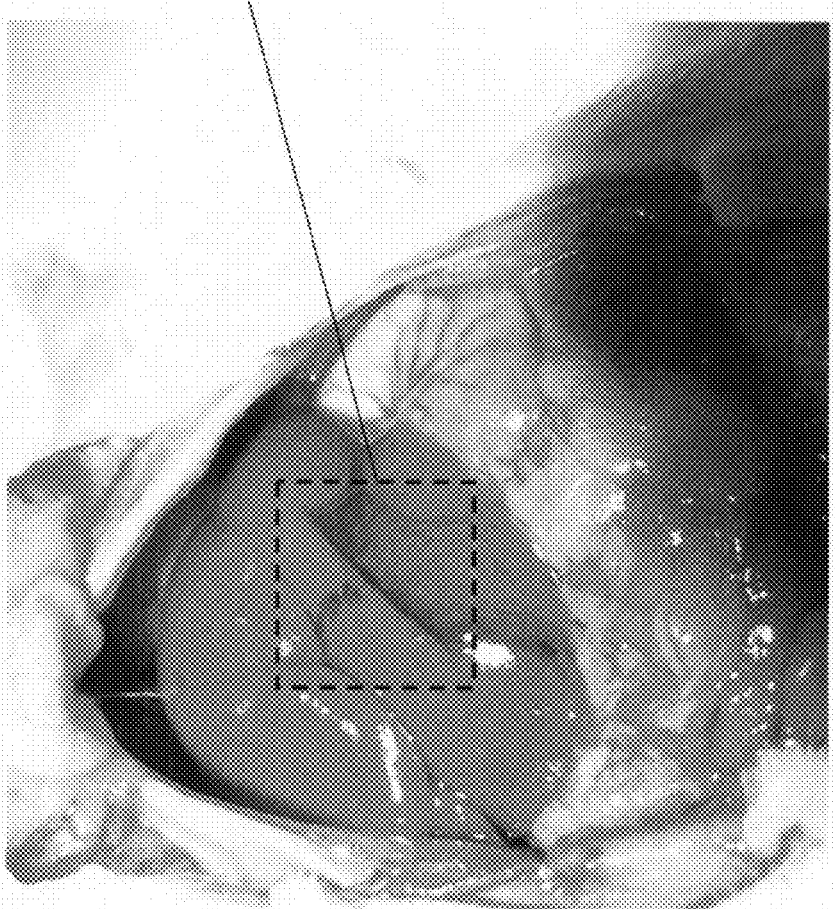
Figure 5B
Figure 5A

Figure 7A
Figure 7B

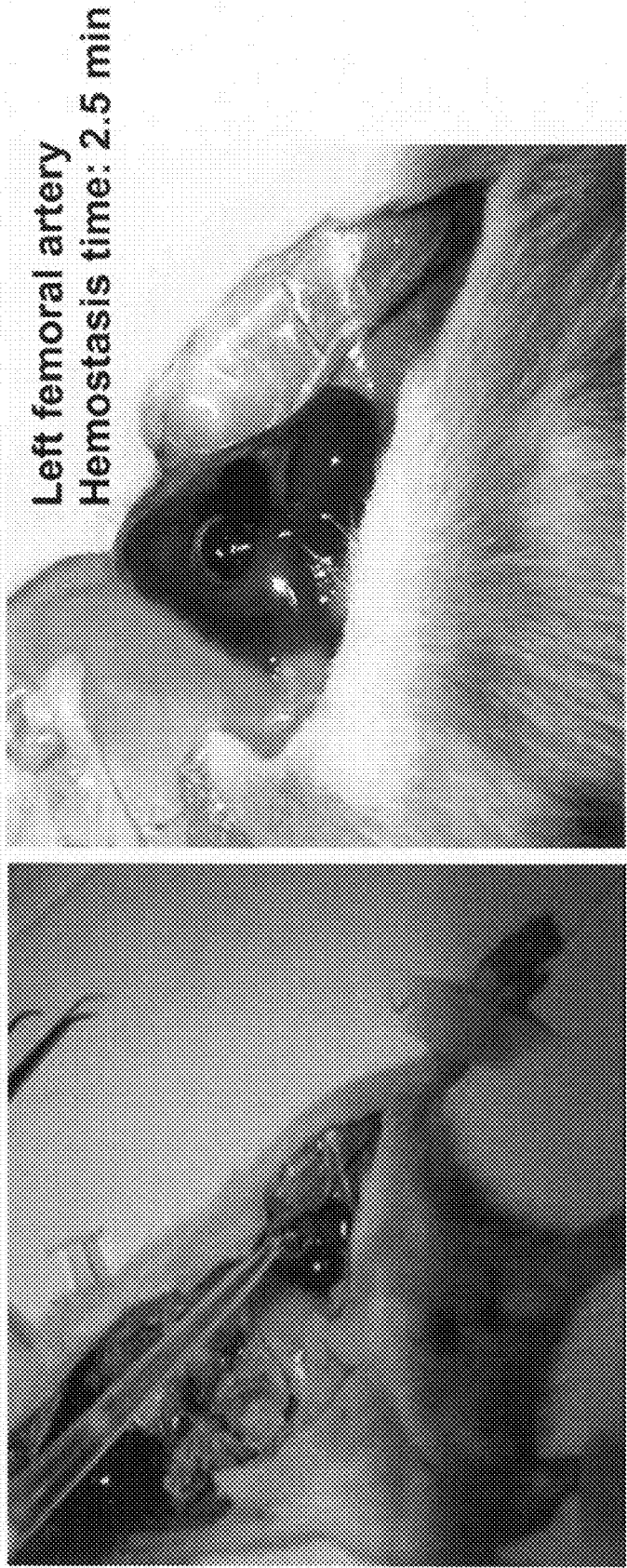

HEMOSTATIC MATERIALS AND DRESSING

CROSS REFERENCE TO RELATED APPLICATION

This U.S. Non-Provisional Application claims priority from U.S. Provisional Application No. 60/875,150, filed on 15 Dec. 2006, which is incorporated herein by reference in its entirety.

FIELD OF THE INVENTION

The present invention relates to hemostatic materials and methods of use thereof.

BACKGROUND OF THE INVENTION

The control of hemorrhage (bleeding) is a critical step in first aid and field trauma care. Unfortunately, the occurrence of excessive bleeding or fatal hemorrhage from an accessible site is not uncommon. (J. M. Rocko et al. (1982). J. Trauma 22:635). Mortality data from the Vietnam War indicates that 10% of combat deaths were due to uncontrolled extremity hemorrhage. Up to one third of the deaths from exsanguination during the Vietnam War could have been prevented by the use of effective field hemorrhage control methods. (SAS/STAT Users Guide, 4th ed. (Cary, N.C.: SAS Institute Inc; 1990)).

Although civilian trauma mortality statistics do not provide exact numbers for prehospital deaths from extremity hemorrhage, case and anecdotal reports indicate similar occurrences (J. M. Rocko et al. (1982). J. Trauma 22:635). These data suggest that a substantial increase in survival can be effected by the prehospital use of a simple and effective method of hemorrhage control. Unfortunately, such a method has not been successfully demonstrated by use of commercially available hemostatic devices.

Most successful high-pressure hemostatic devices currently on the market are nominally, if at all adhesive. Good examples of such devices are the QuikClot® ACS™ (Z-Medica, Wallington, Conn.) and HemCon™ bandage (HemCon, Portland, Oreg.), the two hemostatic devices currently supplied to members of the US armed forces. The mineral zeolite crystals in the QuikClot sponge cause adsorption of the water molecules in the blood, thus concentrating the clotting factors and accelerating blood clotting. The chitosan mixture that makes up the HemCon bandage has a positive charge and attracts red blood cells, which have a negative charge. The red blood cells are drawn into the dressing, forming a seal over the wound, and stabilizing the wound surface.

The HemCon bandage product mentioned above was developed in an attempt to provide pre-hospital hemorrhage control and has already demonstrated limited success in the field. However, the chitosan network that makes up the HemCon bandage can be saturated with blood and fail quickly when faced with brisk flood flow or after 1-2 hours when confronted with moderate blood flow from a wound (B. S Kheirabadi et al. (2005). J. Trauma. 59:25-35; A. E. Pusateri et al. (2006). J. Trauma. 60:674-682). Also, the HemCon bandage patch is available only as a stiff patch that cannot fit easily into irregular wounds, further limiting its utility.

Other polysaccharide-based hemostatic devices that have been suggested for use in hemorrhage control are RDH™ (Acetyl Glucosamine), TraumaDEX™ (MPH), Chitoskin™ (Chitosan & Gelatin), Celox™ (Chitosan Crystals). However, none of these types of bandage have been able to consistently demonstrate sufficient ability to not fail in the face of significant blood flow. As such, they may be considered more appropriate for post-medical care wound management than for emergency trauma care.

QuikClot ACS™, also mentioned above, has also demonstrated efficacy in staunching moderate levels of hemorrhage. However, the water adsorption mechanism of mineral zeolite cannot be effected without the release of a large amount of heat. As such, application of the QuikClot ACS™ results in high temperatures and severe burns at the injury site, which damage surrounding tissue areas and make later medical care far more complicated (A. E. Pusateri et al. (2006). J. Trauma. 60:674-682). Clearly, a hemostatic solution without this significant side effect is more ideal. While QuikClot has developed a mineral mixture that releases less heat upon application, the efficacy of the cooler mixture is insufficient for serious trauma care. Furthermore, neither the original nor cooler mineral mixtures can stop brisk arterial bleeding.

Hemostatic bandages which are adhesive in nature are known in the art, yet have many complications and drawbacks to their use. For example, the widespread hemostatic use of fibrinogen and thrombin was common in the last year of World War II, but was abandoned because of the transmission of hepatitis (D. B. Kendrick, Blood Program in WW II (Washington, D.C.: Office of the Surgeon General, Department of Army; 1989), 363-368).

Fibrinogen dressings were first used by trauma surgeons during World War I when Grey and his colleagues made prepolymerized fibrin sheets and powders. During World War II, fibrin glue was created with prepolymerized Styrofoam-like sheets of fibrin and fibrin films by the United States military and the American Red Cross. Fibrin based dressings show a significant difference in controlling bleeding time and reducing blood loss when compared to a control. (Jackson, M., et al. (1996). J. of Surg. Res. 60:15-22; and Jackson, M., et al. (1997). Surg. Forum. XL, VIII:770-772)

Despite the efficacy of fibrinogen dressings in controlling hemorrhage, the use of fibrinogen dressings was discontinued as blood and serum borne diseases such as hepatitis and HIV were often transmitted since the dressings comprised purified human or animal fibrinogen or other purified blood products. (Holcomb, J. B., et al. (1997). Surgical Clinics of North America. 77:943-952)

In the past few years, however, there has been a renewed interest in fibrin based products for treating wounds as plasma purification techniques have nearly eliminated the risk of blood and serum borne diseases.

A hemostatic sandwich dressing has been described by the US Red Cross, which contains a layer of thrombin sandwiched between layers of fibrinogen (see, e.g., PCT/US99/10952, U.S. Pat. Nos. 6,054,122, 6,762,336). That hemostatic dressing has demonstrated much success in treating potentially fatal trauma wounds (E. M. Acheson. (2005). J. Trauma. 59(4):865-74; discussion 874-5; B. S. Kheirabadi. (2005). J. Trauma. 59(1):25-34; discussion 34-5; A. E. Pusateri. (2004). J. Biomed. Mater. Res. B Appl. Biomater. 15; 70(1):114-21) In fact, in those porcine studies, the fibrin sandwich dressing greatly outperformed the HemCon and QuikClot products in treating potentially fatal trauma wounds, demonstrating a >75% survival rate after 2 hours, versus 0% survival when the standard army field bandage, HemCon bandage, or QuikClot powder was used.

Although such dressings can be used in methods for treating wounded tissue, such conventional sandwich dressings can become delaminated, whereby the edges of the layers of the dressing no longer adhere to each other. Such delamination can result in reduced interaction of the dressing components layers, with decreased effectiveness of the dressing in preventing hemorrhage.

An improved fibrin-based hemostatic sandwich dressing has been described which comprises a plurality of layers that contain resorbable materials and/or coagulation proteins. Specifically, the dressing (see PCT/US03/28100, U.S. patent application Ser. No. 0060/155,234) includes a layer of thrombin sandwiched between a first and second layer of fibrinogen, wherein the layer of thrombin is not coextensive with the first and/or second layer of fibrinogen.

Despite the advances in fibrin wounds dressings, these bandages suffer from many drawbacks. The lyophilized fibrinogen used to make the bandage must be purified from human blood plasma. As this is a costly and delicate procedure, the resulting fibrinogen bandage is extremely expensive to produce and only has a very short shelf life at room temperature. The more fibrinogen that is added to the backing, the better the bandage works in stopping bleeding. However, the more fibrinogen added to the backing, the more costly the bandage. Additionally, high amounts of fibrinogen on the bandage backing may contribute to the fragility of the bandage, making it crumbly and difficult to work with. As a result of these limitations, no efficacious fibrin bandage is commercially available.

Thus, while an advanced fibrin dressing could control hemorrhage without significant side effects and fill the previously mentioned deficiency in active trauma care hemostasis, price and stability limitations prevent any such dressing from becoming commercially viable and being distributed into the field.

Liquid fibrin sealants or glues have been used for many years as an operating room adjunct to hemorrhage control (J. L. Garza et al. (1990). J. Trauma. 30:512-513; H. B. Kram et al. (1990). J. Trauma. 30:97-101; M. G. Ochsner et al. (1990). J. Trauma. 30:884-887; T. L. Matthew et al. (1990). Ann. Thorac. Surg. 50:40-44; H. Jakob et al. (1984). J. Vasc. Surg. 1:171-180). Also, single donor fibrin sealants have also been widely used clinically in various surgical situations. (W. D. Spotnitz. (1995). Thromb. Haemost. 74:482-485; R. Lerner et al. (1990). J. Surg. Res. 48:165-181)

While a number of absorbable surgical hemostats are currently used in the surgical arena, no existing product is sufficiently strong to provide the mechanical and biological support necessary to control severe hemorrhage.

Currently available hemostatic bandages such as collagen wound dressings (INSTAT™, Ethicon, Somerville, N.J., and AVITENE™, C R Bard, Murray Hill, N.J.) or dry fibrin thrombin wound dressings (TACHOCOMB™, Hafslund Nycomed Pharma, Linz, Austria) are restricted to use in surgical applications, and are not sufficiently resistant to dissolution in high blood flow. They also do not possess enough adhesive properties to serve any practical purpose in the stanching of severe blood flow. These currently available surgical hemostatic bandages are also delicate and thus prone to failure should they be damaged by bending or loading with pressure. They are also susceptible to dissolution in hemorrhagic bleeding. Such dissolution and collapse of these bandages may be catastrophic, because it can produce a loss of adhesion to the wound and allow bleeding to continue unabated.

Arterial bleeding is also not manageable with the application of oxidized cellulose (SURGICEL, Ethicon, Somerville, N.J.) or gelatin sponge (SURGIFOAM, Ethicon, Somerville, N.J.) absorbable hemostats. These products are intended to control low-pressure bleeding from bone and epidural venous oozing. Gelatin sponges are not appropriate for high-pressure, brisk flowing arterial bleeding because they do not form a tight bond with the source of bleeding and are thus easily dislodged. Oxidized cellulose is also not appropriate for controlling arterial bleeding because it swells and needs to be removed from the application site when hemostasis is achieved. When the blood flow is too high, too much swelling occurs before hemostasis can be achieved (M. Sabel et al. (2004). Eur. Spine J. 13(1):S97-101).

The most widely used tissue adhesives are generally unfit for use as hemostatic devices, for reasons generally related to inability to be easily prepared and applied in the field. A good example of this is the cyanoacrylate family of topical skin adhesives, such as Dermabond™, Indermil™, Liquiband™ etc. The nature of cyanoacrylate's rapid activation when exposed to air and cyanoacrylate's inability to bind to wet surfaces make cyanoacrylate-based products inappropriate for use in an active hemostatic field dressing.

Gelatin has been used in a variety of wound dressings. Since gelatin gels have a relatively low melting point, they are not very stable at body temperature. Therefore, it is imperative to stabilize these gels by establishing cross-links between the protein chains. In practice, this is usually obtained by treating the gelatin with glutaraldehyde or formaldehyde. Thus, cross-linked gelatin may be fabricated into dry sponges which are useful for inducing hemostasis in bleeding wounds. Commercially available examples of such sponges include Spongostan (Ferrosan, Denmark), Gelfoam (Upjohn, USA), and Surgifoam (Ethicon. Somerville, N.J.). A major disadvantage of these sponges is that the cross-linking agent used (formaldehyde or glutaraldehyde) is toxic for cells. The negative effect of glutaraldehyde cross-linking is exemplified, for instance, by the findings of de Vries et al (Abstract Book of the Second Annual Meeting of the WHS, Richmond, USA, p 51, 1992). These authors showed that glutaraldehyde cross-linked collagen lattices were toxic for cells, whereas the non cross-linked variety was not. Therefore, despite their beneficial hemostatic properties, these products are not very optimal as wound dressings for the treatment of problematic wounds. Consequently, a gelatin-based wound dressing which uses a different, less toxic, cross-linking technology would be very desirable.

Aside from potential toxicity, gelatin networks alone do not provide the mechanical properties necessary for controlling brisk bleeding. They are more appropriate for wound management applications that only require a small amount of fluid absorption. In one study, it was concluded that sheets of glutaraldehyde cross-linked gelatin are more appropriate as a dressing for sustained wound healing, particularly of dystrophic tissue which need longer time. Alternatively, they may be useful as a scaffold for cell attachment, where they can stimulate a poorly reactive microenvironment throughout prolonged in situ presence (M G Tucci. (2001). J. Bioactive & Comp. Polymers. 16(2): 145-157).

Gelatin networks cross-linked with polysaccharides have also been suggested for use in controlling bleeding. These hemostatic compounds are unhindered by the potential toxicity of glutaraldehyde cross-linked gelatin sponges. However, the gelatin-polysaccharide substances generally lack mechanical strength and are intended mainly to control small amounts of oozing fluid during surgery or to limit wound oozing over an extended, post-medical care period.

One example of a gelatin-polysaccharide compound is a gelatin-alginate wound dressing that is cross-linked in situ. Such a dressing has no adhesive function and is mainly used to hold in moisture on the wound site. The dressing swells to 90% of its initial size, which greatly reduces its mechanical strength (B Balakrishnan et al. (2005). Biomaterials. 26(32): 6335-42).

Another, more widespread example, is a cross-linked gelatin-chitosan wound dressing (examples in U.S. Pat. Nos. 6,509,039, 4,572,906). While some have suggested the use of such dressings for trauma care (Chitoskin™), the hemostatic properties of this material are simply insufficient to control high-pressure bleeding. Also, the material swells significantly when confronted with high volumes of bodily fluids. Such dressings are more appropriate for treating chronic wounds and burns.

Yet another example is mentioned (U.S. Pat. No. 6,132, 759) where solubilized gelatin is cross-linked with oxidized dextran. This material is suggested for the covering and long-term treatment of wounds since it demonstrated a high absorptive capacity and favorable controlled release properties for the delivery of therapeutic substances, particularly to wounds.

Currently no material involving cross-linked gelatin networks or networks of other materials cross-linked with gelatin has been able to independently provide hemostasis for brisk internal bleeding. As such, thrombin is frequently added to gelatin matrices to enhance the hemostatic capacity. However, this is only able to increase the hemostatic capacity of gelatin moderately. A study was done comparing the hemostatic capacity of FloSeal gelatin matrix (BioSurgery, Fremont, Calif.) and GelFoam gelatin matrix soaked in active thrombin solution. Aside from the problem caused by antibody responses to thrombin in 3% of patients, neither enhanced hemostatic device was able to stop flow characterized bleed in more than $2/3$ of patients after 5 minutes. Pulsatile arterial bleeding is far more brisk than flow bleeding and would most certainly present a problem for these thrombin-soaked matrices (F A Weaver et al. (2002). Ann. Vasc. Surg. 16(3):286-93).

In any case, there remains a distinct deficiency in trauma care of a novel, active hemostatic field dressing that can control hemorrhage without significant side effects.

SUMMARY OF EMBODIMENTS OF THE INVENTION

There is a need for, and it would be useful to have, a non-toxic adhesive material which could be used for a wide variety of applications, including but not limited to surgical applications, control of hemorrhage and control of bleeding from a wound. There is also a need for, and it would be useful to have, a non-toxic adhesive material which could be used as part of a hemostatic bandage.

The present invention is of an adhesive material which comprises gelatin and a non-toxic material which induces cross-linking of gelatin. Optionally and preferably, the non-toxic material comprises transglutaminase (TG), which may optionally comprise a microbial transglutaminase (mTG). According to some embodiments of the present invention, the adhesive material is provided in a bandage, which is preferably adapted for use as a hemostatic bandage.

According to some embodiments, the adhesive material optionally and preferably comprises non-naturally occurring aggregate forms of: (i) gelatin; (ii) a transglutaminase; wherein the gelatin and transglutaminase are formed into aggregates either separately or together. More preferably, the gelatin and transglutaminase are provided in sufficient quantities to be useful as a hemostatic agent.

According to a preferred embodiment, transglutaminase is present in a composition having a specific activity level of at least about 100 U/gm, although optionally lower activity levels may also be used, for example by optionally adjusting the above described ratios. Such optionally lower activity levels of the composition preferably comprise at least about 20 U/gm, more preferably at least about 40 U/gm, even more preferably at least about 60 U/gm and most preferably at least about 80 U/gm.

The transglutaminase, whether alone or as part of a composition, is preferably added to gelatin in an amount such that the resulting transglutaminase activity in the mixture is preferably from about 25 to about 75 U/g of gelatin and more preferably from about 40 to about 60 U/g of gelatin.

Suitable gelatin and transglutaminase can be obtained by any of the methods known and available to those skilled in the art. Gelatin may optionally comprise any type of gelatin which comprises protein that is known in the art, preferably including but not limited to gelatin obtained by partial hydrolysis of animal tissue and/or collagen obtained from animal tissue, including but not limited to animal skin, connective tissue (including but not limited to ligaments, cartilage and the like), antlers or horns and the like, and/or bones, and/or fish scales and/or bones or other components; and/or a recombinant gelatin produced using bacterial, yeast, animal, insect, or plant systems or any type of cell culture.

According to preferred embodiments of the present invention, gelatin from animal origins preferably comprises gelatin from mammalian origins and more preferably comprises one or more of pork skins, pork and cattle bones, or split cattle hides, or any other pig or bovine source. More preferably, such gelatin comprises porcine gelatin since it has a lower rate of anaphylaxis. Gelatin from animal origins may optionally be of type A (Acid Treated) or of type B (Alkaline Treated), though it is preferably type A.

Preferably, gelatin from animal origins comprises gelatin obtained during the first extraction, which is generally performed at lower temperatures (50-60° C., although this exact temperature range is not necessarily a limitation). Gelatin produced in this manner will be in the range of 250-300 bloom and has a high molecular weight of at least about 95-100 kDa. Preferably, 300 bloom gelatin is used.

A non-limiting example of a producer of such gelatins is PB Gelatins (Tessenderlo Group, Belgium).

According to some embodiments of the present invention, gelatin from animal origins optionally comprises gelatin from fish. Optionally any type of fish may be used, preferably a cold water variety of fish such as carp, cod, or pike, or tuna. The pH of this gelatin (measured in a 10% solution) preferably ranges from 4-6.

Cold water fish gelatin forms a solution in water at 10° C. and thus all cold water fish gelatin are considered to be 0 bloom. For the current invention, a high molecular weight cold water fish gelatin is preferably used, more preferably including a molecular weight of at least about 95-100 kDa. This is equivalent to the molecular weight of a 250-300 bloom animal gelatin. Cold water fish gelatin undergoes thermoreversible gelation at much lower temperatures than animal gelatin as a result of its lower levels of proline and hydroxyproline. Per 1000 amino acid residues, cold water fish gelatin has 100-130 proline and 50-75 hydroxyproline groups as compared to 135-145 proline and 90-100 hydroxyproline in animal gelatins (Haug I J, Draget K I, Smidsrød O. (2004). Food Hydrocolloids. 18:203-213).

A non-limiting example of a producer of such a gelatin is Norland Products (Cranbury, N.J.).

In a preferred embodiment of the invention, the gelatin is purified to remove salts. This can be accomplished according to previously described techniques. One such technique involves forming a 20% w/v solution of gelatin in water and heating it to 60° C. under stirring. The mixture is then let to stand still overnight. The gel obtained is dialysed against repeated changes of deionized water to eliminate salts, stirred and heated to 50° C. to disaggregate the physical network. The final solution was filtered and freeze-dried. (Crescenzi V, Francescangeli A, Taglienti A. (2002). Biomacromolecules. 3:1384-1391). Alternatively, the gelatin can be desalted by size exclusion column.

According to some embodiments of the present invention, a recombinant gelatin is used. Recombinant gelatins are currently commercially produced by FibroGen (San Francisco, Calif.). The currently preferred method is using a recombinant yeast system (*Pichia Pastoris*) to express specified fragments of Type I, alpha1 human sequence collagen.

In an optional but preferred embodiment of the present invention, recombinant gelatins are fully synthetic molecules, containing no contaminating components from humans or any animals. By "synthetic" it is meant that the gelatin is preferably produced according to a method selected from chemical synthesis, cell free protein synthesis, cell tissue culture, any type of bacterial, insect or yeast culture, or in plants. The use of synthetic gelatins eliminates many of the variables and drawbacks associated with tissue-derived materials, including provoking unwanted immune responses. For example, fish gelatins demonstrate high allergenicity and animal gelatins demonstrate low-moderate allergencity, while recombinant gelatins can have zero allergenicity. Additionally, recombinant gelatins present no threat of virus transmission. In human safety studies, no adverse events related to recombinant gelatin were found.

Methods of creating recombinant gelatins and the benefits of their use are fully described in U.S. Pat. Nos. 6,413,742 and 6,992,172, which are hereby incorporated by reference as if fully set forth herein.

Recombinant gelatins can be produced to be highly (99%) purified. Recombinant gelatin production allows for the optional production of gelatins with at least one defined and predetermined characteristic, including but not limited to defined molecular weights, pI (isoelectric point), guaranteed lot-to-lot reproducibility, and the ability to tailor the molecule to match a specific application.

An example of tailoring a molecule to match a specific application has been previously described wherein a gelatin was created to be highly hydrophilic (Werten M W T, et al. (2001). Protein Engineering. 14 (6): 447-454). Optionally and preferably a gelatin according to the present invention comprises a gelatin having at least one adjusted, tailored or predetermined characteristic.

Non-limiting examples of other types of characteristics which may optionally be so tailored according to the present invention include undergoing or not undergoing thermoreversible gelation. Recombinant gelatins can be created to undergo thermoreversible gelation or not undergo thermoreversible gelation. A gelatin that has one or more beneficial characteristics of natural animal gelatin but does not undergo thermoreversible gelation has tremendous amount of utility in enabling the cross-linking of gelatin by other means at temperatures at which it would normally undergo thermoreversible gelation. Such a gelatin is also encompassed by some embodiments of the present invention.

According to preferred embodiments of the present invention, a suitable in vitro culturing system is used to produce the recombinant gelatin. In addition to the use of recombinant methylotrophic yeast systems for the production of recombinant gelatin, other organisms have been used.

Recombinant, gelatin-like proteins have been expressed in *Escherichia coli* though expression levels usually obtained in *E. coli* are rather low and purification of the intracellularly produced protein can be difficult. *Bacillus brevis* has been used for the expression of gelatin-like proteins wherein sequence stretches were selected from natural collagen genes and polymerized to form semi-synthetic gelatin (Werten M W T, et al. Secreted production of a custom-designed, highly hydrophilic gelatin in *Pichia pastoris*. Protein Engineering, Vol. 14, No. 6, 447-454, June 2001).

Additional successful efforts at producing recombinant gelatin have included the production of recombinant gelatin using mammalian and insect cells. Collagen and gelatin have also been expressed in transgenic tobacco plants, transgenic mice. A transgenic silkworm system has been used to produce a fusion protein containing a collagenous sequence. These systems lack sufficient endogenous prolyl hydroxylase activity to produce fully hydroxylated collagen, which can be overcome by over-expression of prolyl hydroxylase (Olsen D, et al. Recombinant collagen and gelatin for drug delivery. Adv Drug Deliv Rev. 2003 Nov. 28; 55(12):1547-67). Plant based systems may also optionally be used; for example a collaboration between Iowa State University and Fibrogen is developing the expression of gelatin in transgenic corn.

The gelatin employed in the hemostatic dressing can be a gelatin complex or any gelatin, or a derivative or metabolite thereof, or a gelatin produced according to a single process or a plurality of processes. For example, the gelatin may optionally comprise gelatin type A or gelatin type B, or a combination thereof.

The transglutaminase may optionally comprise any plant, animal, or microbe derived transglutaminase, preferably other than blood derived Factor XIII. Preferably, microbial transglutaminase derived from *Streptoverticillium mobaraensis* is used.

The transglutaminase may optionally be in a composition comprising at least one other substance, such as a stabilizer or filler for example. Non-limiting examples of such materials include maltodextrin, hydrolyzed skim milk protein or any other protein substance, sodium chloride, safflower oil, trisodium phosphate, sodium caseinate or lactose, or a combination thereof.

Although the optimal pH for activity of crude transglutaminase is 6.0, it also functions with high activity in the range of pH 5.0 to pH 8.0. Therefore, a composition according to the present invention for hemostasis preferably has a pH value in a range of from about 5 to about 8.

Transglutaminase features a negative temperature coefficient. Over the temperature range of the transglutaminase activity, it takes a shorter time to react at higher temperatures and longer amount of time to start functioning at lower temperatures. The following table shows different reaction times at different temperatures comparing the same reaction grade as the reaction at 50° C., pH 6.0 that occurs in 10 minutes:

TABLE 1

| reaction temperature of transglutaminase | | | | | |
|---|---|---|---|---|---|
| Temperature | 5° C. | 15° C. | 20° C. | 30° C. | 40° C. |
| Time (minutes) | 240 | 105 | 70 | 35 | 20 |

Non-limiting examples of commercially available transglutaminase products include those produced by Ajinomoto Co. (Kawasaki, Japan). A preferred example of such a product from this company is the Activa TG-TI (In Europe: Activa WM)—Ingredients: mTG and maltodextrin; Activity: 81-135 U/g of Activa. Other non-limiting examples of suitable products from this company include Activa TG-FP (ingredients: hydrolyzed skim milk protein, mTG; activity: 34-65 U/g of Activa TG-FP); Activa TG-GS (ingredients: sodium chloride, gelatin, trisodium phosphate, maltodextrin, mTG, and safflower oil (processing aid); activity: 47-82 U/g of Activa TG-GS); Active TG-RM (In Europe: Activa EB)—ingredients: sodium caseinate, maltodextrin, and mTG; activity: 34-65 U/g of Activa; Activa MP (ingredients: mTG, Lactose and Maltodextrin; activity: 78-126 U/g of Activa).

Other non-limiting examples of commercially available transglutaminase products include those produced by Yiming Biological Products Co. (Jiangsu, China). A preferred example of such a product from this company is the TG-B (ingredients: 1% mTG, 99% co-protein; activity: 80-130 U/g of TG-B). Other non-limiting examples of suitable products from this company include TG-A (ingredients: 0.5% mTG, 99.5% co-protein; activity: 40-65 U/g of TG-A).

For both examples, preferred transglutaminase products are those with the highest specific activity and simplest co-ingredients, as they are believed (without wishing to be limited by a single hypothesis) to have the best reactivity upon application and a lower potential for undesired side effects.

According to some embodiments, transglutaminase can be used in the form of any of the above described compositions, optionally including any of the commercially available mixtures that include transglutaminase.

In another embodiment, any of the above transglutaminase mixtures may optionally be purified by means of gel filtration or by cation-exchange chromatography according to previously described methods to remove their carrier proteins and/or carbohydrates (Bertoni F, Barbani N, Giusti P, Ciardelli G. Transglutaminase reactivity with gelatine: perspective applications in tissue engineering *Biotechnol Lett* (2006) 28:697-702) (Broderick E P, et al. Enzymatic Stabilization of Gelatin-Based Scaffolds J Biomed Mater Res 72B: 37-42, 2005).

Regardless, the activity of transglutaminase is preferably measured prior to use and/or manufacture of a composition according to the present invention with a transglutaminase reactivity assay. Such an assay may optionally include but is not limited to the Hydroxamate Method, Nessler's Assay, a Colorimetric Assay, or any other assay of transglutaminase activity (see for example Folk J E, Cole P W. Transglutaminase: mechanistic features of the active site as determined by kinetic and inhibitor studies. *Biochim Biophys Acta.* 1966; 122:244-64; or the Nessler Assay as described in: Bertoni F, Barbani N, Giusti P, Ciardelli G. Transglutaminase reactivity with gelatine: perspective applications in tissue engineering *Biotechnol Lett* (2006) 28:697-702).

In general, the purity and/or quality of the gelatin and/or the transglutaminase for use in the hemostatic composition will be of an appropriate purity known to one of ordinary skill in the relevant art to lead to efficacy and stability of the protein.

When acted upon by a transglutaminase, gelatin, which is a denatured form of the protein collagen, undergoes rapid crosslinking to form a vibrant gel. The gelation process that takes place is extremely similar to the natural late stage clotting cascade that fibrin undergoes when it comes into contact with Factor XIII and calcium. Furthermore, the resulting gel demonstrates adhesive capacity very similar to, if not greater than, that of fibrin glues. (M. K. McDermott, Biomacromolecules. 2004 July-August; 5(4): 1270-9). As such, there have been efforts to utilize the gelatin-mTG mixture as a low-cost replacement for fibrin glues or sealants in surgical areas that have been aided by the use of such adhesives.

Unlike a clotted fibrin network, the gelatin-TG network has an additional benefit in that it can be dissolved specifically using a specified protease that is not otherwise physiologically reactive (T. Chen, Biomacromolecules. 2003 November-December; 4(6):1558-63). Thus, while a gelatin-mTG hemostatic sandwich dressing can replicate the performance of a fibrin-thrombin hemostatic sandwich dressing, it can also be removed as desired without complication.

Beyond its application as a hemostatic field-dressing for trauma care, the gelatin-TG based hemostatic device of the present invention has great potential in controlling brisk, arterial bleeding during surgery.

Efforts to find clinical applications for the adhesive capacity of gelatin-TG mixture have centered on very specific surgical applications for tissue adhesives. For example, adhesive use of the gelatin-TG compound was demonstrated in vivo in a rat retina model, where a drop of gelatin-TG mixture was used for retinal attachment (T. Chen, J Biomed Mater Res B Appl Biomater. 2006 May; 77(2):416-22).

These efforts are not to be confused with efforts that have been made to utilize the physiological nature of the gelatin-TG gel in using it as a scaffold for cell therapy inside the body (U.S. Pat. No. 5,834,232. Also Ito A, J Biosci & Bioeng. 2003; 95(2): 196-99. Also, Broderick E P, J Biomed Mater Res B Appl Biomater. 2005 Jan. 15; 72(1):37-42). These studies, though they further emphasize the safety of physiological use of the gelatin-TG mixture, are unrelated to tissue adhesion.

Use of the gelatin-TG mixture as an adhesive marks a significant advance from a number of well-documented attempts to use transglutaminases, included TG, independently as surgical adhesives (U.S. Pat. No. 5,736,132, U.S. 61,908,196, among many). When used independently, transglutaminases can only bind specific types of tissue that contain transglutaminase specific protein chains. Additionally, their use is unwieldy and unsafe since free transglutaminase in the body can create complications related to unwanted clotting or adhesion. The addition of gelatin enables transglutaminase to be used in a contained, pre-mixed fashion.

According to other embodiments, the invention also includes methods for treating wounded tissue in a patient, which comprise applying any of the novel hemostatic compositions described herein to wounded tissue. In such methods, the hemostatic compositions can be hydrated with liquids that are exogenous to the wounded tissue, or can be hydrated with liquids that are endogenous to the wounded tissue.

The present invention overcomes the drawbacks of the background art. Prior attempted solutions used many forms of modified and unmodified gelatin networks for mild to moderate hemostasis. However, a method of forming a strongly cross-linked gelatin network that can control brisk bleeding, arterial hemorrhage has been lacking. A method, such as gelatin-TG gelation, that can form a strong gelatin network in vivo increases the mechanical strength of a gelatin matrix and makes it suitable for controlling high-pressure arterial bleeding. Aside from the improved method of cross-linking, the herein invention involves many other innovations that provide it with advantages over existing gelatin-based hemostatic materials. A non-limiting, illustrative list is provided below:

1) Gelatin and TG in lyophilized form, reconstitutable by the blood have greater shelf life and in situ crosslinking, which may have a beneficial effect on hemostasis.
2) Gelatin and TG in layered, lyophilized form provided more rapid reconstitution, which necessary for high pressure blood flow environment.

3) The application of the gelatin-TG mixture for a hemostatic trauma care bandage or absorbable, surgical wound management hemostat provide a greater combination for hemostasis, as reliance for initial hemostasis is not solely on the gelatin matrix. By utilizing specialized bandage backing or matrix materials, the blood flow from a wound can be slowed so as to give the gelatin-TG mixture a slightly extended amount of time to adhere tightly to the tissue surrounding a wound site.

It is to be understood that both the foregoing general description and the following detailed description are exemplary and explanatory only and are intended to provide further explanation of the invention as claimed.

Unless defined otherwise, all technical and scientific terms used herein have the same meaning as is commonly understood by one of skill in the art to which this invention belongs. All patents, patent applications, and publications mentioned herein are incorporated herein by reference.

"Patient" as used herein refers to human or animal individuals in need of medical care and/or treatment.

"Wound" as used herein refers to any damage or trauma to any tissue of a patient that results in the loss of blood (or optionally other bodily fluids) from the circulatory system. The tissue can be an internal tissue, such as an organ or blood vessel, or an external tissue, such as the skin. The loss of blood can be internal, such as from a ruptured organ, or external, such as from a laceration. A wound can be in a soft tissue, such as an organ, or in hard tissue, such as bone. The damage may have been caused by any agent or source, including traumatic injury, infection or surgical intervention. The damage can be life-threatening or non-life-threatening.

"Stability" as used herein refers to the retention of those characteristics of a material that determine activity and/or function.

As used herein, "about" means plus or minus approximately ten percent of the indicated value.

Other features and advantages of the invention will be apparent from the following detailed description, and from the claims.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 5A and 5B are color photographs showing the formation of the gel and also induction of hemostasis (FIG. 5A shows the entire area while FIG. 5B shows a portion of the area, magnified for further details);

FIG. 6A shows lack of clot formation after application of control solution, while FIGS. 7A-7D are illustrative photographs of the artery as it was being cut (7A); the cut artery, bleeding profusely (7B); application of the composition of the present invention to the cut artery (7C); and hemostasis, with formation of a biomimetic clot (7D).

DETAILED DESCRIPTION OF EMBODIMENTS OF THE INVENTION

The present invention is of an adhesive material which comprises gelatin and a non-toxic material which induces cross-linking of gelatin. Optionally and preferably, the non-toxic material comprises transglutaminase (TG), which may optionally comprise any type of calcium dependent or independent transglutaminase (mTG), which may for example optionally be a microbial transglutaminase. According to some embodiments of the present invention, the adhesive material is provided in a bandage, which is preferably adapted for use as a hemostatic bandage.

According to some embodiments, the adhesive material optionally and preferably comprises non-naturally occurring aggregate crystallized forms of: (i) gelatin; (ii) a transglutaminase; wherein the gelatin and transglutaminase are formed into crystals either separately or together. More preferably, the gelatin and transglutaminase are provided in sufficient quantities to be useful as a hemostatic agent.

Various amounts of each and their ratios were previously described. The transglutaminase content may optionally be increased to increase the rate of reaction or decreased to enhance safety. According to some embodiments of the present invention, a 15-30% solution of gelatin is preferably applied, followed by a 15-30% solution of transglutaminase. The concentration of gelatin per area of bandage depends upon a number of factors, including but not limited to the final construction of the bandage, materials employed and so forth.

The principles and operation of the present invention may be better understood with reference to the drawings and the accompanying description.

Referring now to the below illustrative Examples, various compositions according to the present invention were constructed and tested for their ability to reduce bleeding and to induce hemostasis. The tested compositions were found to be very strong and to be able to stop bleeding, even arterial bleeding, in an experimental animal.

Example 1

Preparation of Illustrative Adhesive

This Example relates to the preparation of an illustrative, non-limiting adhesive composition according to the present invention. For this Example, calcium independent microbial transglutaminase (Lot No. L-04207, Ajinomoto USA, Chicago, Ill.) was used with a specific activity level of 100 U/gm. Also the tested gelatin was Gelatin type A, 300 Bloom from porcine skin (Sigma-Aldrich, St. Louis, Mo.).

The following method was used to prepare the illustrative adhesive: 20% w/w gelatin in PBS (phosphate buffered saline; 20 g gelatin into 80 g of PBS) was prepared. Next a 20% w/v mTG solution was prepared in PBS (1 gm mTG into 5 mL PBS). Then, 5 g of gelatin solution was mixed with 0.5 mL of mTG solution (in other words 10:1 ratio).

Figure 1:
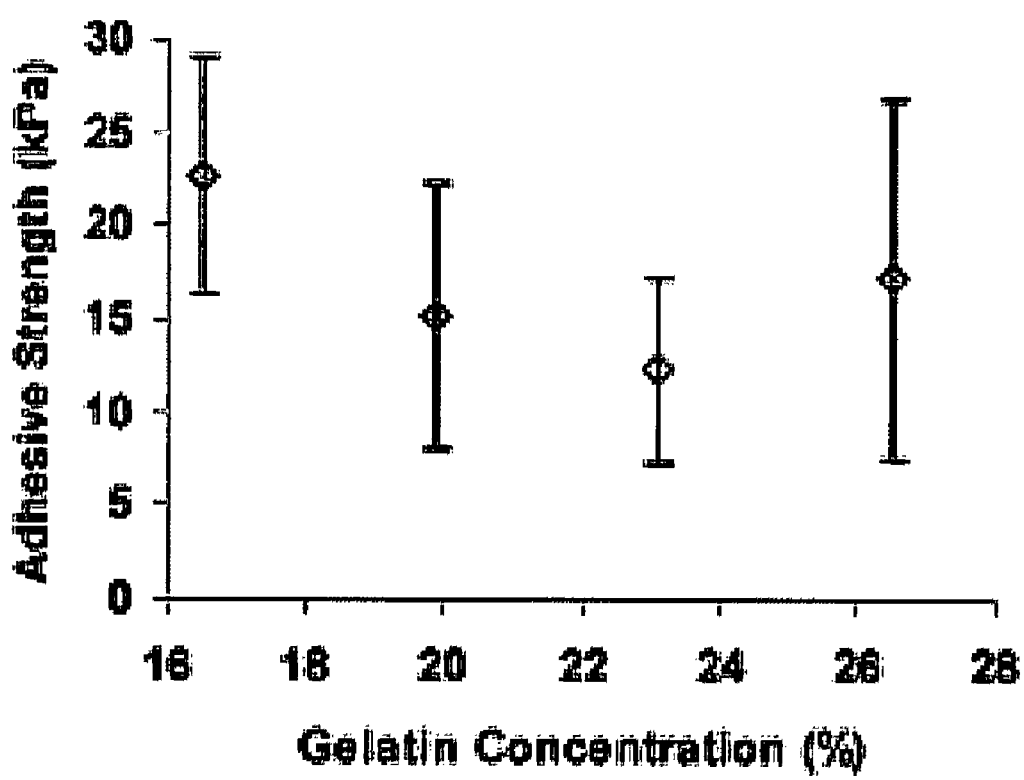
FIG. 1 is a graph showing the effect of different percentages of a tested gelatin on wound strength.

FIG. 1 shows the effect of different percentages of gelatin on the adhesive strength of the adhesive. The adhesive strengths were measured by adhering a porcine skin sample to a second such sample, placing a 47.5 g weight on the joint, and then submerging it immediately in water for 120 minutes. After the submersion period, tension was applied at 5 mm/min to determine the ultimate adhesion strength (Mcdermott et al. Biomacromolecules 2004, 5, 1270-1279).

Figure 2:
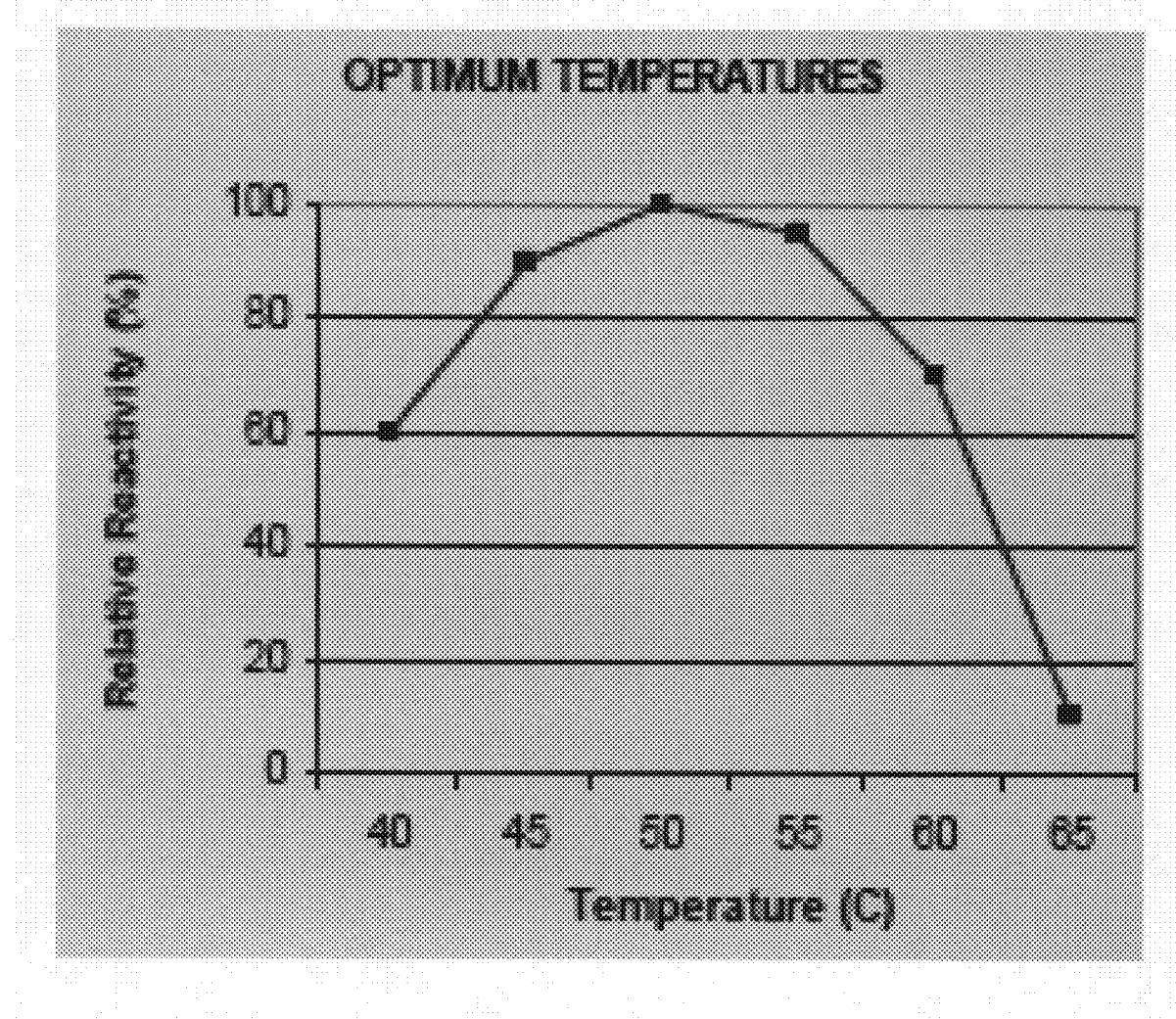
FIG. 2 shows effect of temperature on activity of transglutaminase (Temperature Range tested was 32 to ~150° F.; optimum range was 122-131° F. (50-55° C.))

As demonstrated in FIG. 2, the optimum reactivity level of microbial transglutaminase is in the range of 50-55° C. At the physiological level of 37° C., the reactivity level is only about 60% of the optimum level but would still be sufficient for hemostatic treatment.

Example 2

In Vitro Burst Pressure Test

This Example demonstrates the ability of a composition according to the present invention to withstand bursting as a proxy for its ability to withstand high-pressure arterial blood flow. A burst pressure system was developed, as describe below, to mimic high pressure blood flow, with warm PBS used in the place of blood to put pressure on a wound in a porcine skin sample. Withstanding 200 mmHg of pressure for 2 minutes was considered the success criteria as physiological blood pressure is nearly always lower than 200 mmHg. These burst test results demonstrated that compositions according to the present invention are suitable for treatment of blood flow, including high pressure arterial flow.

Most samples (8/10) withstood a pressurization of 200 mmHg for 2 minutes. Those that did not pass were likely related to human or system error. The average burst pressure was 320±50 mmHg but this number is conservative since samples that did not burst were assigned a numerical value of 354 mmHg, as this was the maximum pressure measurable by the experimental apparatus. These results demonstrate the capability of the adhesive composition according to some embodiments of the present invention to be used for hemostatic purposes, even under rigorous testing conditions.

Materials

Gelatin (type A from porcine, Bloom value 300) was obtained from Sigma-Aldrich (St. Louis, Mo.). The calcium-independent microbial transglutaminase (mTG) mixture TG-TI was obtained from Ajinomoto and was used without further purification. This enzyme is reported by the manufacturer to have a specific activity of 100 U/gm. Porcine skin tissue was purchased from a local grocery store.

Sample Preparation

The porcine skin was treated with dilute NaOH for 1 h before cutting into a disk shape, with a diameter of about 6-6.5 cm. The fat on the skin was removed with a scalpel. A 2-mm hole was punched at the center of the skin section to simulate a wound. The skin was washed with copious amounts of water and PBS buffer, and stored in a Petri dish with about 1 ml PBS buffer to keep the skin wet until use. For all experiments described herein, Dulbecco's Phosphate Buffered Saline was used with a pH of 7.4 for the PBS buffer.

Gelatin solution (25% w/w) in PBS buffer was freshly prepared each day and stored at 65° C. before use. The mTG (20% w/w) stock solution in PBS buffer was prepared and aliquotted into 2 ml vials, and stored at −18° C. The enzyme solution was thawed at room temperature before use.

The skin surface was touch-dried with a lab tissue wipe before the adhesive was applied. The adhesive was prepared in a 2 ml vial by mixing 1 ml gelatin and 0.5 ml mTG. Two different compositions were prepared. Composition "A" used transglutaminase from Ajinomoto, while composition "B" used transglutaminase from (Yiming Biological Products Co. (Jiangsu, China); the preferred product as described above). 0.6 ml of the resultant mixture (an exemplary tissue adhesive composition according to the present invention) was applied onto the porcine skin over the hole. After applying the adhesive, the skin tissue was incubated at 37° C. for 30 min. Burst tests were performed immediately after incubation.

Burst Test

The home-built device was equilibrated in warm buffer (~44° C.) before assembly. After quickly assembling the incubated skin into the device, about 50 ml 42° C. PBS buffer was poured into the device on top of the skin tissue. A nitrogen stream was manually controlled to increase the pressure. The overall procedure for the burst test was as follows:

Step 1—Increase pressure to 200 mmHg and hold for 2 minutes;

Step 2—Increase pressure to 300 mmHg and hold for 2 minutes;

Step 3—Increase pressure to >354 mmHg (maximum pressure measurable).

As controls, pure gelatin solution was applied onto the skin and allowed to gel (i.e., set) at room temperature for 30 min by forming a physical gel. Gelatin-Warm refers to the use of 42° C. buffer solution that can melt the physical gelatin gel.

Results

Figure 3:
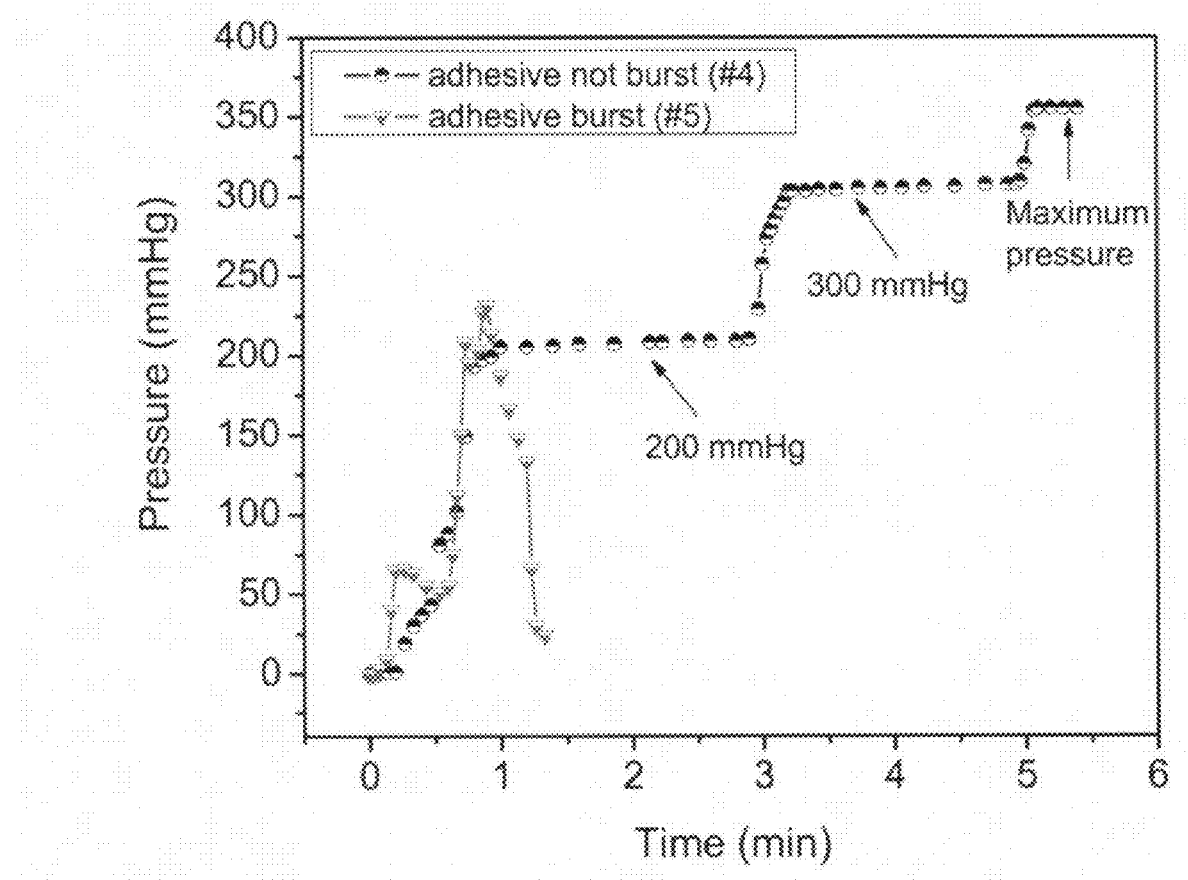
FIG. 3 shows representative burst pressure measurements of tissue adhesives based on composition A.

FIG. 3 shows representative burst pressure measurements of tissue adhesives based on composition A. Data are shown for samples #4 and #5 in FIG. 3. A summary of the burst test results for composition A is given in Table 2, while the full list of samples is shown in Table 3.

TABLE 2

Summary of burst test results for composition A

| | |
|---|---|
| Total number of samples tested | 10 |
| No burst | 5 |
| Burst after Step #2 | 1 |
| Burst after Step #1 | 2 |
| Burst during Step #1 | 2 |
| Average burst pressure* | 320 ± 50 mmHg |

*A numerical value of 354 mmHg (maximum pressure measurable) was adopted for "No failure" samples.

TABLE 3

Burst test results of samples of composition A

| Sample # | 200 mmHg | 300 mmHg | Burst pressure (mmHg) | Burst type | Notes |
|---|---|---|---|---|---|
| 1 | 2 min | — | 325 | cohesive | |
| 2 | 2 min | 2 min | >354 | | |
| 3 | 2 min | 2 min | >354 | | |
| 4 | 2 min | 2 min | >354 | | |
| 5$^a$ | 30 sec | — | 232 | cohesive | Device leak |
| 6 | 2 min | 2 min | >354 | | |
| 7 | 2 min | 2 min | 348 | cohesive | |
| 8 | 2 min | — | 250 | cohesive | 44° C. PBS |
| 9 | 2 min | 2 min | >354 | | |
| 10 | 10 sec | — | 245 | cohesive | 44° C. PBS |
| Controls: Gelatin-Warm | | | | | |
| 13 | — | — | 181 | melted | 42° C. PBS |
| 14 | — | — | 45 | melted | 37° C. PBS |
| 15 | — | — | 93 | melted | |

TABLE 3-continued

Burst test results of samples of composition A

| Sample # | 200 mmHg | 300 mmHg | Burst pressure (mmHg) | Burst type | Notes |
|---|---|---|---|---|---|
| 16 | — | — | 105 | melted | |
| 17 | — | — | 84 | melted | |
| 18 | — | — | 45 | melted | |
| 19 | — | — | 15 | melted | |
| 20 | — | — | 140 | melted | |

[a]At ~200 mmHg device started to leak. Tightening the device increased the pressure but may also distort the skin too much to cause the adhesive failed at 232 mmHg.

Figure 4:
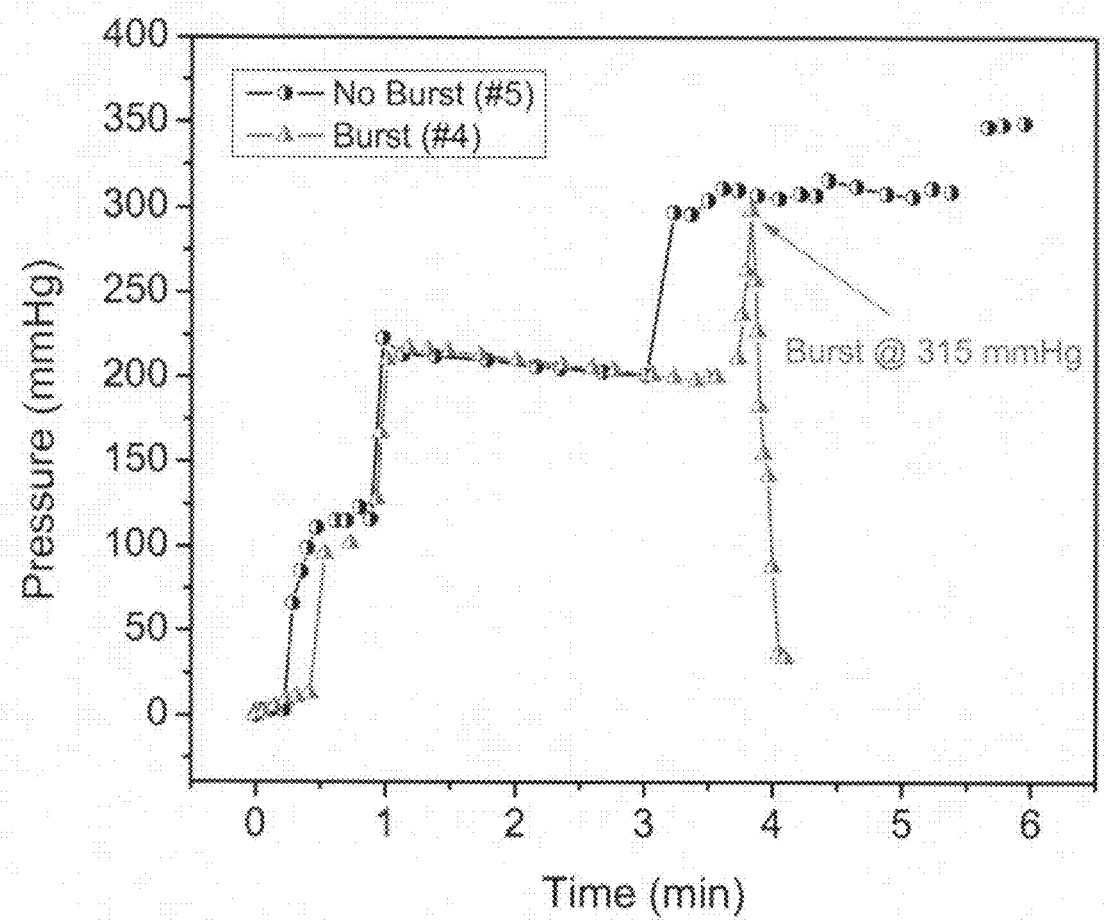
FIG. 4 shows representative burst pressure measurements of tissue adhesives based on composition B.

FIG. 4 shows representative burst pressure measurements of tissue adhesives of composition B. Data are shown for samples #4 and #5 in FIG. 4. Results for the full list of samples is shown in Table 4.

TABLE 4

Burst test results of samples of composition B.

| Sample # | 200 mmHg | 300 mmHg | Burst pressure (mmHg) | Burst type | Notes |
|---|---|---|---|---|---|
| 1* | | 2 min | max | | |
| 2 | 2 min | 2 min | max | | |
| 3* | | | max, 2 min | | |
| 4 | 2 min | — | 315 | cohesive | 44° C. PBS |
| 5 | 2 min | 2 min | max | | |

*The pressures of these samples were inadvertently set above 200 mmHg since the pressure was controlled manually and there is no pressure release valve.

Example 3

Hemostasis in a Rat Model

This Example provides an initial in vivo demonstration of a gelatin-mTG composition according to the present invention for achieving hemostasis in a live animal. The rat was an adult female Syrian Rat.

Materials

A gelatin solution was used which featured 25% w/w gelatin (porcine, type A, 300 bloom from Sigma-Aldrich (St. Louis, Mo.)) in PBS. The solution was mixed by mixing heated (50° C.) PBS into gelatin powder as it was manually stirred using a spatula. Prior to application, gelatin solution was stored in capped 5 mL syringes submerged in a 50° C. water bath to maintain its liquid form.

The transglutaminase (mTG) solution featured 20% w/w microbial transglutaminase (Activa WM, Ajinomoto™) in PBS. The mTG solution was maintained at room temperature.

Prior to application, 1 mL of gelatin solution was added to 0.5 mL of mTG solution in a 2 mL eppendorf tube. The tube was inverted 2-3 times to mix the solutions and then solution was applied to the wound site using a 1 mL pipette tip. This was the experimental solution.

For the control solution, the protocol was repeated but without the addition of mTG solution, such that gelatin alone was administered.

For both experimental and control applications, pipette tips were cut approximately ½ cm from the end in order to expand the opening and enable the passage of the viscous gelatin-mTG solution.

Liver Wound

For both the experimental and control applications, the left lobe of the liver was cut using a scalpel in the rostral-to-caudal direction, creating a 1 cm long, ½ cm deep sagittal cut. After approximately 10 seconds of bleeding, cotton gauze was used to remove the accumulated blood immediately prior to application of either the gelatin (control) or gelatin-mTG (experimental) solutions.

First, the experimental solution was applied to a cut on the left side of the lobe. A gel formed approximately two minutes after application and bleeding was completely stopped in less than about 2.5 minutes after application. After 5 minutes, the tissue was vigorously agitated and tension was applied across the wound site using forceps, yet the gel remained intact and the wound closed. FIG. 5 is a photograph showing the formation of the gel and also induction of hemostasis (FIG. 5A shows the entire area while FIG. 5B shows a portion of the area, magnified for further details).

Figure 6A:

Afterward, the control solution was applied to a cut on the right side of the lobe. No gel formed and the solution was mostly washed out of the wound site by the blood flow. Even after 6-7 minutes, no clot was formed and the liver continued bleeding (FIG. 6A).

Figure 6B:
FIG. 6B shows gelation of the experimental solution and hemostasis.

The control solution was removed and the experimental solution was then applied to the wound site without removing the accumulated blood. Though the accumulated blood clearly hindered gelation of the experimental solution, a gel still formed that greatly slowed blood flow after about one minute and completely stopped it after 4.5 minutes (FIG. 6B). Thus, clearly the composition of the present invention is able to slow blood flow and to induce hemostasis even in the presence of accumulated blood.

Femoral Artery Cut

The left femoral artery of the rat was severed using a scalpel. After approximately 10 seconds of heavy bleeding, cotton gauze was used to remove the accumulated blood immediately prior to application of the gelatin-mTG (experimental) solution. As the solution was applied, blood mixed with the experimental gel as it was undergoing gelation. Under these rigorous conditions, the gel still completely stopped the bleeding in less than three minutes. After 5 minutes, the gel was manually tested using forceps. Gel was noticeably less stiff and less adherent when it was mixed heavily with blood but still formed a strong clot over the severed artery site. FIGS. 7A-D show photographs of the artery as it was being cut (7A); the cut artery, bleeding profusely (7B); application of the composition of the present invention to the cut artery (7C); and hemostasis, with formation of a biomimetic clot (7D).

The right femoral artery of the rat was then severed using a scalpel. After approximately 10 seconds of bleeding, cotton gauze was used to remove the accumulated blood immediately prior to application of the gelatin-mTG (experimental) solution. Heavy bleeding was observed but was almost immediately halted by the gel and bleeding was completely stopped in less than one minute. The gel held very strongly and the blood that was trapped by gel was readily observable. After 5 minutes, the gel was manually tested using forceps. It was adhered very strongly to the tissue in the area of the artery, despite the presence of trapped blood in the formed gel.

Thus, clearly compositions according to the present invention are able to slow down the rate of bleeding and to induce hemostasis in an in vivo model, even in the presence of accumulated blood and/or heavy bleeding (as for example from an artery and/or a vascularized organ including but not limited to liver, stomach, kidneys, heart, lung and/or skin for example).

Example 4

Hemostasis in a Porcine Model

This example provides an initial in vivo demonstration of a gelatin-mTG composition according to the present invention for achieving hemostasis in a large animal model. The potential for hemostasis utility in a large animal model was clearly demonstrated.

Materials

The gelatin solution featured 25% w/w gelatin (porcine, type A, 300 bloom from Sigma-Aldrich (St. Louis, Mo.)) in PBS (pH 7.4) and was prepared as described herein. PBS was stirred continuously at 60° C. using a hot plate magnetic stirrer while gelatin powder was gradually added. Manual stirring using a glass stick was performed occasionally to increase the dissolution rate of the powder and to achieve a homogenous solution. Throughout the entire experiment, the gelatin solution was stored in a thermal bath adjusted to ~50° C. to maintain its liquid form and prevent the formation of physical gel, except when in actual use.

The mTG solution featured 20% w/w microbial transglutaminase (Activa WM, Ajinomoto™) dissolved in PBS (pH 7.4). It was prepared as follows. Room temperature (RT) PBS solution was stirred using a magnetic stirrer and mTG powder was gradually added. Throughout the entire experiment the mTG solution was kept in a thermal bath adjusted to ~30° C., except when in actual use.

An adult, female pig weighing 45 kg was put under general anesthesia prior to the start of the experiment. Throughout the experiment the pig was ventilated and its vital signs were monitored.

Prior to application to the wound site as described below, the gelatin-mTG solution according to the present invention was prepared and an applicator was used to place the sealant onto the wound site. Several different applicators were examined as the bandage's supportive material. Unless otherwise stated, before its immediate application onto wound site, 6 mL of novel surgical sealant solution were spread over the applicator and left to cool for 1 min at RT. This sealant-containing pad is considered the "bandage prototype". For the "control bandage", a similar protocol was followed, but with the control solution being spread over the applicator.

Novel Surgical Sealant Solution—A 2:1 gelatin to mTG mixture was prepared. Unless otherwise stated, the mixture was prepared by adding 2 mL mTG solution to 4 mL gelatin solution in a 15 mL tube and the tube was inverted 5 times to mix the solutions.

Control Solution—For the control solution the procedure described for Novel Surgical Sealant preparation was repeated, except that PBS alone was used instead of the mTG solution. Accordingly, gelatin was diluted in a 2:1 ratio with PBS solution (pH 7.4), submerged in a ~30° C. thermal bath. Unless otherwise stated, the mixture was prepared by adding 2 mL PBS solution to 4 mL gelatin solution in a 15 mL tube and the tube was inverted 5 times to mix the solutions.

Applicators were used as follows:
1. A 4 cm×4 cm cotton gauze pad.
2. A 4 cm×4 cm diaper. The solution was spread on the plastic, non-absorbing side of the diaper.
3. A silicon mold.
4. A 4 cm×4 cm diaper placed inside a silicon mold. The solution was spread on the plastic, non-absorbing side of the diaper.
5. A transparent flexible plastic mold with high margins.
6. Direct application of the sealant on the wound site using a syringe or spilling from a 15 mL tube.

Application of the novel surgical sealant in this study was accomplished by the surgeon manually placing the sealant over the wound site using different applicators. If needed, cotton gauze was used to remove the accumulated blood immediately prior to application. Hemostatic pressure was applied on the inverse side of the bandage for 3 minutes. After 3 minutes, the surgeon relieved pressure and wound site was observed for hemostasis. If full hemostasis did not occur, the wound site was closed by accepted surgical hemostatic techniques. Application of the control solution followed the same technique, with accepted hemostatic techniques being immediately applied if hemostasis was not observed after the control bandage was removed.

Gluteal Muscle Wound

The animal was placed in a prone position and the skin above the gluteal muscles was removed. Overall, 7 experiments were conducted in which hemostasis and tissue adhesion were examined. Unless otherwise stated, in each trial a 3 cm×3 cm square of muscle was cut 2 cm deep into the muscle, using a #15 scalpel. Excess blood was removed from the wound area as needed and the novel surgical sealant solution or control solution were applied as previously described.

Tables 5 and 6 summarize and describe the experimental procedure and results of each of the experiments. Table 5 relates to hemostasis while Table 6 relates to tissue adhesive properties.

Turning first to hemostasis, the control solution was applied to a wound site using a cotton gauze pad (Table 5, Control #1). The control solution was applied on the cotton gauze and left to cool for 1 min 20 sec prior to its immediate application. The wound site showed poor bleeding and 2 min after applying the control bandage, complete hemostasis was observed. This is probably due to the hemostatic pressure applied over the site while applying the bandage. No biomimetic clot was observed at the wound site.

The experiment was repeated in a different wound site, with the difference being that the applicator used was a diaper and the control solution was left to cool for 30 sec prior to its application (Table 5, Control #2). The wound site showed very little bleeding and 2 min after applying the control bandage, complete hemostasis was observed. As in the previous case, this is probably due to the hemostatic pressure applied over the site while applying the bandage. No biomimetic clot was observed at the wound site.

Due to the small amount of bleeding observed during the first two control experiment, the experiment was repeated, with the exception being that a deeper, 4 cm deep cut, was made (Table 5, Control #3). Consequently, heavy bleeding was observed. The control solution was applied over a diaper and left to cool for 50 s. The surgeon removed excess blood from the wound area and applied the control bandage. After 3 min, bleeding decreased but full hemostasis was not observed.

The control solution was removed from the wound site created at the former experiment using a cotton gauze pad. Bleeding was still observed. The novel surgical sealant was applied to the wound area to achieve hemostasis (Table 5, Sealant #1). The sealant solution was placed over a diaper, left to cool for 1 min and applied over the wound site. After 3 min, complete hemostasis was observed. The sealant formed a biomimetic clot over the wound site. The gel was agitated using forceps and strong adherence to the tissue was observed. The gel was removed after applying some force and appeared as a film. Thus, these results demonstrate the hemostatic properties of the composition according to the present invention.

TABLE 5

Gluteal Muscle

| Experiment | RT (°C.) | Heart Rate | Application Technique | Description | Time to Hemostasis (min) | Results |
|---|---|---|---|---|---|---|
| Control #1 | 21 | 99 | Cotton gauze pad | The wound site showed little bleeding following the incision. Prior to applying, control solution was placed over the applicator and left to cool for 1 min 20 sec. | 2 | Note that following the incision, little bleeding from the wound area was observed. Hemostasis was achieved, likely by just applying pressure over the wound site. |
| Control #2 | 21 | 98 | Diaper | The wound site showed little bleeding following the incision. Control solution was placed over the applicator and left to cool for 30 sec prior to applying onto the wound site. | 2 | Note that following the incision, little bleeding from the wound area was observed. Hemostasis was achieved, likely by just applying pressure over the wound site. |
| Control #3 | 22 | 98 | Diaper | 4 cm deep cut was made. Massive bleeding was observed. Control bandage was left to cool for 50 sec. Prior to its application over the wound site, excess blood was removed. | — | The surgeon applied hemostatic pressure due to the massive bleeding. After 3 min, bleeding decreased but did not stop. |
| Sealant #1 | 22 | 99 | Diaper | Control solution was removed from the wound site performed for control #3. Excess blood was removed. The sealant was placed over the bleeding wound site. | 3 | A strong biomimetic clot was formed over the wound site. Complete hemostasis and strong adhesion of the sealant were observed. |

After demonstrating the hemostasis capacity of the sealant in a gluteal muscle model, tissue adhesion was examined (Table 6). Surgical incisions were made to lift a segment of tissue from the muscle bed, opening a wound site.

At the first adhesion experiment (Table 6, Sealant #2), the sealant was directly applied over the wound site and the surgeon applied strong immediate pressure on the upper part of the tissue for 3 min, displacing all of the sealant from the wound site and resulting in no adhesion.

The experiment was repeated with the exception that following the application of the sealant, the surgeon applied only moderate pressure (Table 6, Sealant #3). After 3 min it appeared the tissues adhered. When the upper part of the tissue was agitated, a moderate amount of resistance was experienced to its complete removal.

The experiment was repeated with special care taken to not displace the sealant from the wound site upon application of pressure (Table 6, Sealant #4). On a different wound site, the sealant was applied on both parts of the tissue and left for 10 sec. Then, the upper side of the tissue was replaced and moderate pressure was applied. After 3 min, strong tissue adhesion was observed. A significant amount of force was needed to then separate the adhered tissues.

TABLE 6 tissue adhesion

| Experiment | RT (°C.) | Heart Rate | Application Technique | Description | Tissue Adhesion | Results |
|---|---|---|---|---|---|---|
| Sealant #2 | 23 | 99 | Direct application from a tube | Excess blood was removed using a cotton gauze pad. The sealant was placed over the wound site and immediate displacing pressure was applied by the surgeon. | N/A | No sealant remained in the wound site. |

TABLE 6-continued tissue adhesion

| Experiment | RT (° C.) | Heart Rate | Application Technique | Description | Tissue Adhesion | Results |
|---|---|---|---|---|---|---|
| Sealant #3 | 23 | 94 | Direct application from a tube | Excess blood was removed using a cotton gauze pad. The sealant was placed at the wound site and the surgeon applied moderate pressure. | + | Adhesion was observed with slight resistance. |
| Sealant #4 | 24 | 95 | Direct application from a tube | The sealant solution was placed over the wound site, on both parts of the tissue and left for ~10 sec. then the upper side of the tissue was replaced and very low pressure was applied. | + | Strong adhesion was observed. Only after applying intensive force the tissue was removed. |

Hemostasis in Liver

The pig was placed supine and its liver was exposed through a midline laparotomy. Serial cuts were performed to remove progressively deeper biopsies of the liver, consequently exposing larger blood vessels. Overall, 5 biopsies were preformed. When needed, cotton gauze was used to remove the accumulated blood immediately prior to application of the composition according to the present invention.

At the first series of biopsies the control bandage was applied with hemostatic pressure on the inverse side of the bandage for 3 minutes. After 3 minutes, the surgeon relieved pressure and wound site was observed for hemostasis. When full hemostasis did not occur, another biopsy was preformed, followed by application of the novel surgical sealant. Again, the sealant was applied with hemostatic pressure on the inverse side of the bandage for 3 min and then hemostasis was examined. When full hemostasis was observed, a deeper liver biopsy was removed and the experiment was repeated with the sealant. This demonstrated the hemostasis capability of the sealant for higher blood pressures. Table 7 summarizes the experimental procedure and results of each experiment.

A 4 cm deep biopsy was removed from the left lobe of the liver (Table 7, Control #1). The control solution was applied over a diaper placed in a silicon mold and left to cool for 1 min. The control bandage was applied over the wound site with hemostatic pressure. After 3 min, pressure was removed and no hemostasis was observed.

After no hemostasis was achieved by applying the control bandage, a 1 cm deeper biopsy was removed and left to bleed for 30 sec. The experiment was then repeated with the novel sealant (Table 7, Sealant #1). The novel sealant was placed on the diaper in a silicon mold and after 1 min applied to the wound site with hemostatic pressure. After 3 min, the pressure was relieved, the prototype bandage was peeled, and hemostasis was examined. The sealant created a visible biomimetic film. Hemostasis was achieved but was not complete since the sealant did not cover the entire wound. It was visible that areas covered with the sealant stopped bleeding. When the biomimetic film was removed after several minutes, bleeding resumed.

Next, a 1 cm deeper biopsy was removed, resulting in heavy bleeding. The experiment was repeated with the exception that a silicon mold was used as the applicator and excess blood was removed prior to application (Table 7, Sealant #2). The surgeon then applied pressure to the wound site for 3 min. When the surgeon removed his hand, a biomimetic clot was visible over the wound site. The pressure of the blood pushing against the biomimetic clot was apparent and after several more minutes, blood breached from the rim of the biomimetic sealant. The breach was through a side part of the wound site that was not covered by the sealant. This indicated that, at this stage, the hemostatic ability of the sealant is related to covering the entire wound site.

To avoid breaching, the former experiment was repeated; with the exception that a larger amount of sealant was applied over the wound site (Table 7, Sealant #3). A 0.5 cm deeper biopsy was removed from the liver lobe. 9 mL sealant was applied over the wound site with pressure. Unfortunately, during application, nearly all of the sealant dripped off to the sides of the wound site, leaving no discernable sealant on the wound site after pressure was applied by the surgeon.

The experiment was repeated (Table 7, Sealant #4). Another 1 cm biopsy was removed and massive bleeding was observed. This time, 15 mL of sealant was applied over the wound site using a transparent plastic mold with high margins to keep the sealant in place. The sealant was placed on the applicator and left to cool for 1 min 20 sec. The sealant was applied over the wound site and 4 min later, a thick layer of biomimetic clot was observed and complete hemostasis was achieved. 50 min later the tissue was reexamined and hemostasis was still observed. This indicated the strong hemostatic capacity of the sealant when sufficient sealant is applied to a wound site and maintained in place. The formed biomimetic film was difficult to remove as it was strongly adhered to the tissue surface and removal of the film resulted in a small amount of bleeding.

TABLE 7

Hemostasis in Left Liver Lobe

| Experiment | RT (°C.) | Heart Rate | Application Technique | Description | Time to Hemostasis (min) | Results |
|---|---|---|---|---|---|---|
| Control #1 | 25 | 87 | Diaper in a silicon mold | 4 cm biopsy was removed. The control solution was placed over the applicator, left for 1 min and applied with hemostatic pressure over the wound site for 3 min. | — | Massive bleeding after application. No hemostasis or biomimetic film was observed. |
| Sealant #1 | 24 | 86 | Diaper in a silicon mold | Another 1 cm biopsy was removed and left to bleed for 30 sec. | 3 | The novel sealant partially stopped the massive bleeding by creating a biomimetic film. Complete hemostasis was not achieved since the sealant did not cover the entire wound. |
| Sealant #2 | 24 | 86 | A silicon mold | Another 1 cm biopsy was removed and excess blood was removed. The sealant was applied with hemostatic pressure. | 3 | The sealant did not cover the entire wound area, though hemostasis was achieved where the sealant was present. |
| Sealant #3 | 24 | 84 | Silicon mold | Another 0.5 cm biopsy was removed and excess blood was removed prior to application of the sealant. 9 mL of sealant were applied. | — | All sealant was displaced during the application process. |
| Sealant #4 | 24 | 80 | Transparent, flexible plastic mold with high margins | Another 1 cm biopsy was removed. 15 mL sealant were applied over the applicator, left 1 min 20 sec to cool and then placed over the wound site. | 4 | A thick layer of biomimetic clot was formed. Complete hemostasis was achieved. 50 min later the tissue was reexamined and hemostasis was still observed. The formed film was hard to remove and after removal some bleeding continued. |

Hemostasis in Kidney

Next, a severe, high pressure bleeding model was tested. A ~5 cm biopsy was removed from the upper pole of the right kidney of the pig using surgical shears, resulting in high-pressure bleeding. 9 mL of novel surgical sealant solution was prepared, placed in a silicon mold, left to stand for 1 min, and then applied over the trimmed kidney. Though pressure was maintained over the wound site, the high pressure blood flow quickly flushed all sealant from the wound area. Hemostasis was eventually achieved using surgical hemostats. This confirmed that the partial kidney biopsy is an appropriate high-pressure blood flow model for the testing of the hemostatic potential of a surgical sealant. It is believed that with superior application methods, the novel surgical sealant tested in this study can achieve hemostasis under the vigorous conditions of a partial biopsy of the kidney. Table 8 summarizes the experimental procedure and results of this experiment.

TABLE 8

| | | | | Time to | |
|---|---|---|---|---|---|
| Experiment | RT (° C.) | Heart Rate | Application Technique | Description | Hemostasis (min) | Results |
| Sealant # 1 | 24 | 85 | Silicon mold | ~5 cm biopsy was removed and massive bleeding was observed. 9 mL sealant solution was placed over the applicator, left for 1 min and then applied over the trimmed kidney. | — | All sealant was flushed from the applicator; none remained on the wound site. |

Hemostasis in Femoral Artery

Next, the ability of the composition of the present invention to induce hemostasis in wounds or trauma to an artery, specifically the femoral artery, was examined. The animal's right femoral artery was exposed. Then, a circular 2 mm longitudal cut was preformed using a surgical blade. Massive bleeding was observed and therefore a hemostat was used. Excess blood was removed using a cotton gauze pad immediately prior to application of the sealant. About 9 mL Novel Surgical Sealant were prepared and applied using a syringe over the wound area. After 4 min, the hemostat was gently removed and hemostasis via the sealant was examined. A biomimetic clot was observed and complete hemostasis was reached. Table 9 summarizes the experimental procedure and results of this experiment.

TABLE 9 hemostasis in femoral artery

| Experiment | RT (° C.) | Heart Rate | Application Technique | Description | Time to Hemostasis (min) | Results |
|---|---|---|---|---|---|---|
| Sealant # 1 | 24 | 96 | A syringe | 2 mm punch was performed and a hemostat was used to stop the massive bleeding. ~9 mL of sealant solution were applied over the wound site using a syringe. After 4 min the hemostat was gently removed. | 4 | After removal of the hemostat complete hemostasis was observed. The sealant created a biomimetic clot over the wound site that managed to block the massive bleeding. |

While the claimed invention has been described with reference to the foregoing detailed description thereof and preferred embodiments, the foregoing description is intended to illustrate and not limit the claimed invention, aspects of which are defined by the scope of the appended claims. Other aspects, advantages, and/or modifications are within the scope of those claims.

What is claimed is:

1. A method of treating a wounded tissue, comprising applying to said tissue a composition comprising gelatin and a non-toxic cross-linking agent, wherein said non-toxic cross-linking agent comprises transglutaminase, wherein said transglutaminase is included as part of a transglutaminase composition and the weight ratio of gelatin to transglutaminase composition is in a range of from about 1:10 to about 100:1, wherein activity of said transglutaminase in the gelatin-transglutaminase composition is at least about 40 U/g of gelatin, and wherein said gelatin and said transglutaminase are mixed before being applied to said tissue in liquid form; inducing hemostasis in said wound; and forming a biomimetic clot through in-situ cross-linking of said gelatin to said tissue by said transglutaminase and through formation of an in-situ matrix by said cross-linking.

2. The method of claim 1, wherein said transglutaminase composition has a specific activity level of at least about 40 U/gm.

3. The method of claim 2, wherein said transglutaminase composition has a specific activity level of at least about 80 U/gm.

4. The method of claim 1, wherein said activity is from about 40 to about 60 U/g of gelatin.

5. The method of claim 1, wherein said transglutaminase comprises a plant, animal, or microbe derived transglutaminase other than blood derived Factor XIII.

6. The method of claim 5, wherein said composition has a pH in a range of from about 5 to about 8.

7. The method of claim 1, wherein said gelatin is produced from animal origin, recombinant origin or a combination thereof.

8. The method of claim 7, wherein said animal origin is selected from the group consisting of fish and mammals.

9. The method of claim 8, wherein said mammal is selected from the group consisting of pigs and cows.

10. The method of claim 8 wherein said gelatin is of type A (Acid Treated) or of type B (Alkaline Treated).

11. The method of claim 10, wherein said gelatin comprises high molecular weight gelatin.

12. The method of claim 1, wherein said wounded tissue is selected from the group consisting of surgically cut tissue and traumatized tissue.

13. The method of claim 1, wherein said wound has at least two edges and said treating said wounded tissue further comprises adhering at least two edges of said wound with said composition.

14. The method of claim 1, wherein said tissue comprises a damaged blood vessel and wherein said biomimetic clot is formed at said damaged blood vessel.

15. A method of treating a wounded tissue, comprising applying to said tissue a composition comprising providing gelatin and a non-toxic cross-linking agent as separated components, wherein said non-toxic cross-linking agent comprises transglutaminase, wherein said transglutaminase is included as part of a transglutaminase composition and the weight ratio of gelatin to transglutaminase composition is in a range of from about 1:10 to about 100:1, and wherein activity of said transglutaminase in the gelatin-transglutaminase composition is at least about 40 U/g of gelatin; mixing said gelatin and said transglutaminase to form a mixture; upon mixing said gelatin and said transglutaminase to form a mixture, applying said mixture to said wounded tissue; inducing hemostasis in said wounded tissue; and forming a biomimetic clot through in-situ cross-linking of said gelatin to said tissue by said transglutaminase and through formation of an in-situ matrix by said cross-linking.

* * * * *